United States Patent
Feitsma et al.

(10) Patent No.: US 9,402,363 B1
(45) Date of Patent: Aug. 2, 2016

(54) PERONOSPORA RESISTANCE IN SPINACIA OLERACEA

(71) Applicant: RIJK ZWAAN ZAADTEELT EN ZAADHANDEL B.V., De Lier (NL)

(72) Inventors: Johannes Geert Jan Feitsma, De Lier (NL); Vincent Laurens Adrianus Kock, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 14/947,092

(22) Filed: Nov. 20, 2015

(51) Int. Cl.
*A01H 5/12* (2006.01)
*C12Q 1/68* (2006.01)

(52) U.S. Cl.
CPC ............... *A01H 5/12* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2013/0230635 A1* | 9/2013 | Den Braber | A01H 1/04 426/615 |
| 2015/0240256 A1* | 8/2015 | Brugmans | A01H 5/12 800/265 |

FOREIGN PATENT DOCUMENTS

WO   WO 2013/064436   5/2013

OTHER PUBLICATIONS

Feng et al., Plant Disease 98(1):145-52 (2014).*
Feng et al., Identification of New Races and Deviating Strains of the Spinach Downy Mildew Pathogen Peronospora farinosa f. sp. *spinaciae*, Plant Disease, Jan. 2014 vol. 98 No. 1, 145-152.
Feng et al., Construction of a Spinach Bacterial Artificial Chromosome (BAC) Library as a Resource for Gene Identification and Marker Development, Plant Mol Biol Rep (2015) 33:1996-2005.

* cited by examiner

*Primary Examiner* — Amjad Abraham
*Assistant Examiner* — Russell Boggs
(74) *Attorney, Agent, or Firm* — Vedder Price P.C.; Thomas J. Kowalski; Deborah L. Lu

(57) ABSTRACT

The present invention relates to a spinach plant which may comprise an allele conferring resistance to downy mildew, propagation material of said spinach plant, a cell of said spinach plant, seed of said spinach plant, and to harvested leaves of said spinach plant. The invention further relates to use of a spinach plant in breeding to confer resistance against downy mildew.

9 Claims, No Drawings

SEQUENCE LISTING

<160> NUMBER OF SEQ ID NOS: 8

<210> SEQ ID NO 1
<211> LENGTH: 79
<212> TYPE: DNA

<213> ORGANISM: Spinacia oleracea

<400> SEQUENCE: 1
gaggtggtta tggaggagta cacaacaagg tacacttcac atctccacca cccccttcat    60
tccataccga aaacttgcc    79

<210> SEQ ID NO 2
<211> LENGTH: 79
<212> TYPE: DNA
<213> ORGANISM: Spinacia oleracea

<400> SEQUENCE: 2
gaggtggtta tggaggagta cacaacaagg taaacttcac atctccacca cccccttcat    60
tccataccga aaacttgcc    79

<210> SEQ ID NO 3
<211> LENGTH: 100
<212> TYPE: DNA
<213> ORGANISM: Spinacia oleracea

<400> SEQUENCE: 3
gctcagtgtc atctttatgc agaagtatat catagaattg tcaaaaaatg atccgatcta    60
gaccaacctg ataaaaaaaa tcggaagtgg cttgatctcg    100

<210> SEQ ID NO 4
<211> LENGTH: 104
<212> TYPE: DNA
<213> ORGANISM: Spinacia oleracea

<400> SEQUENCE: 4
gctcagtgtc atctttatgc agaagtatat catagaattg tcaaaaaatg atccgatcga    60
tctagaccaa cctgataaaa aaaatcggaa gtggcttgat ctcg    104

<210> SEQ ID NO 5
<211> LENGTH: 119
<212> TYPE: DNA
<213> ORGANISM: Spinacia oleracea
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other

<400> SEQUENCE: 5
gcagcatgat tgacaacttg gtttaacttt tgctgcnana nctcttttt ctttcttgta    60 tcctctttta acttccattc aaaagaatt ttgtggttta ggagttgtag tggtggggt    119

<210> SEQ ID NO 6
<211> LENGTH: 119
<212> TYPE: DNA
<213> ORGANISM: Spinacia oleracea
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base

```
<222> LOCATION: (39)..(39)
<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other

<400> SEQUENCE: 6
gcagcatgat tgacaacttg gtttaactt tgctgcnana nctctttttt ctttcttgta      60
tcctctttta acttccatcc aaaaagaatt ttgtggttta ggagttgtag tggtggggt     119

<210> SEQ ID NO 7
<211> LENGTH: 143
<212> TYPE: DNA
<213> ORGANISM: Spinacia oleracea
<220> FEATURE:
<221> NAME/KEY: modified_base
<222> LOCATION: (49)..(49)
<223> OTHER INFORMATION: a, c, t, g, unknown or other

<400> SEQUENCE: 7
gtcgatctga caagtttgag atgtataagt ttttctaggg atcaatttng tatcaaatga     60
gcggtttaat ttcaagtctt gtaatcaaat aaaagtctga ttttgtcaaa tctatcaaaa    120
tcataaacaa atatcaagag atg                                            143

<210> SEQ ID NO 8
<211> LENGTH: 143
<212> TYPE: DNA
<213> ORGANISM: Spinacia oleracea
<220> FEATURE:
<221> NAME/KEY: modified_base
<222> LOCATION: (49)..(49)
<223> OTHER INFORMATION: a, c, t, g, unknown or other

<400> SEQUENCE: 8
gtcgatctga caagtttgag atgtataagt ttttctaggg atcaatttng tatcaaatga     60
gcggtttaat ttcaagtcgt gtaatcaaat aaaagtctga ttttgtcaaa tctatcaaaa    120
tcataaacaa atatcaagag atg                                            143
```

PERONOSPORA RESISTANCE IN SPINACIA OLERACEA

SEQUENCE LISTING

The instant application contains a Sequence Listing which has been submitted electronically in ASCII format and is hereby incorporated by reference in its entirety. Said ASCII copy, created on Dec. 14, 2015, is named 43104.00.2220_SL.txt and is 2,921 bytes in size.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated herein by reference, are hereby incorporated herein by reference, and may be employed in the practice of the invention.

FIELD OF THE INVENTION

The present invention relates to a spinach plant which may comprise an allele conferring resistance to downy mildew, the invention also relates to propagation material of said spinach plant, to a cell of said spinach plant, to seed of said spinach plant, and to harvested leaves of said spinach plant. The invention further relates to use of a spinach plant in breeding to confer resistance against downy mildew.

BACKGROUND OF THE INVENTION

Spinach (*Spinacia oleracea* L.) is a flowering plant from the Amaranthaceae family that is grown as a vegetable. The consumable parts of spinach are the leaves and petioles from the vegetative stage. Spinach is sold loose, bunched, in pre-packed bags, canned, or frozen. There are three basic types of spinach: industry-, fresh and Asiatic spinach. Within these types three different leaf types can be recognised: savoy, semi-savoy and smooth types. Savoy has crinkly and curly leaves. Flat or smooth leaf spinach has broad, smooth leaves. Semi-savoy is a variety with slightly crinkled leaves. The main market for spinach is baby-leaf. Baby spinach leaves are often of the flat-leaf variety and usually the harvested leaves are not longer than about eight centimeter. These tender, sweet leaves are sold loose rather than in bunches. They are often used in salads, but can also be lightly cooked.

Downy mildew is a major threat for spinach growers, because it affects the harvested plant parts, namely the leaves. In spinach, downy mildew is caused by the oomycete *Peronospora farinosa* f. sp. *spinaciae* (formerly known as *P. effusa*). Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f. sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of ≥80%, and within 6 and 13 days after infection mycelium growth can be observed. Oospores of *P. farinosa* can survive in the soil for up to 3 years, or as mycelium in seeds or living plants.

In recent years various resistance genes have been identified that provide spinach plants with a resistance against downy mildew. However, it has been observed that previously resistant spinach cultivars can again become susceptible to the fungus. Investigations revealed that the cultivars themselves had not changed, and that the loss of downy mildew resistance must therefore be due to *P. farinosa* overcoming the resistance in these spinach cultivars. The downy mildew races (also called physios, strains or isolates) that were able to infect resistant spinach cultivars were collected in a differential reference set, which can be used to test spinach cultivars for resistance. A differential set also exists of spinach cultivars (hybrids) that have different resistance patterns to the currently officially denominated pathogenic *Peronospora farinosa* f. sp. *spinaciae* races.

To date 15 pathogenic races of spinach downy mildew (Pfs) have been officially identified and characterized, and many new candidates are observed in the field. The 15 officially recognised races of *Peronospora farinosa* f. sp. *spinaciae*, are designated Pfs: 1 to Pfs: 15 (Irish et al. Phtypathol. Vol. 98 pg. 894-900, 2008; Plantum NL (Dutch association for breeding, tissue culture, production and trade of seed and young plants) press release, "Benoeming van Pfs: 14, een nieuwe fysio van valse meeldauw in spinazie", Sep. 19, 2012; Report Jim Correl (Univ. Arkansas) and Steven Koike (UC Cooperative Extension, Monterey County), "Race Pfs: 14—Another new race of the spinach downy mildew pathogen", Sep. 18, 2012; Plantum NL press release, "Denomination of Pfs: 15, a new race of downy mildew in spinach", Sep. 2, 2014). Races 4 to 14 were identified between 1990 and 2012, while only recently another new *Peronospora* isolate has been identified, termed UA4712, which subsequently has been officially named Pfs: 15 by the International Working Group on *Peronospora* (IWGP) (Plantum NL (Dutch association for breeding, tissue culture, production and trade of seed and young plants) press release, "Denomination of Pfs: 15, a new race of downy mildew in spinach", Sep. 2, 2014. All 15 officially recognized Pfs races are publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

These newly identified *Peronospora* races can break the resistance of many spinach varieties that are currently used commercially worldwide, and they thus pose a serious threat to the productivity of the spinach industry. Spinach reference variety Viroflay is susceptible to all known races, while cultivars such as Lion and Lazio show resistance to multiple races. However, it is crucial to stay at the forefront of developments in this field, as *Peronospora* continuously develops the ability to break the resistances that are present in commercial spinach varieties. For this reason new resistance genes are very valuable assets, and they form an important research focus in spinach breeding. The goal of spinach breeders is to rapidly develop spinach varieties with a resistance to as many *Peronospora* races as possible, including the latest identified races, before these races become wide-spread and can threaten the industry.

Recently new *Peronospora farinosa* f.sp. *spinaciae* isolates have been identified, termed UA1014 and US1508. Along with the 15 other officially recognized *Peronospora* races these isolates are available from Rijk Zwaan, Burgemeester Crezeelaan 40, 2678 KX De Lier. Isolate UA1014 is also available from the Department of Plant Pathology, University of Arkansas, Fayetteville, Ark. 72701, USA. Both *Peronospora farinosa* f.sp. *spinaciae* isolates UA1014 and US1508 have been reported to the NAK Tuinbouw, Sotaweg 22, 2371 GD Roelofarendsveen as candidates for official denomination as new *Peronospora farinosa* f.sp. *spinaciae* races.

Citation or identification of any document in this application is not an admission that such document is available as prior art to the present invention.

SUMMARY OF THE INVENTION

No resistance gene is known that confers resistance to the new isolate UA1014 as well as Pfs:15 and/or Pfs:14. In the absence of a suitable resistance source to provide spinach varieties with resistance to the full spectrum of *Peronospora* races, certain isolates may spread during the following growing seasons and cause great damage to the worldwide spinach industry in the immediate future.

It is thus desired to identify new R-genes conferring resistance to newly emerging *Peronospora* strains and develop new plant varieties carrying those genes. Therefore, it is the object of the invention to provide an allele of an R-gene in spinach, conferring resistance to various *Peronospora* races, including the one that has been most recently identified, which enables the easy transfer of this broad resistance pattern to other spinach plants.

Thus, the invention relates to a spinach plant which may comprise an allele of an R-gene, wherein said allele confers resistance to at least *Peronospora farinosa* f. sp. *spinaciae* races Pfs:1, Pfs:2, Pfs:3, Pfs:4, Pfs:5, Pfs:6, Pfs:9, Pfs: 11, Pfs: 12, Pfs:13, Pfs:14, Pfs: 15 and UA1014, and does not confer resistance to *Peronospora farinosa* f. sp. *spinaciae* race Pfs:7, and wherein said allele is as found in a plant grown from a seed of which a representative sample was deposited with the NCIMB under NCIMB accession number 42466.

The present invention relates to a new allele of an R-gene herein named R15 which confers resistance onto spinach plants to downy mildew races Pfs: 1, Pfs:2, Pfs:3, Pfs:4, Pfs:5, Pfs:6, Pfs:9, Pfs: 11, Pfs:12, Pfs:13, Pfs:14, Pfs:15 and UA1014. In the prior art no spinach cultivars are known that have a resistance against this combination of downy mildew races, that is conferred by a single resistance gene. The current invention thus represents an important step forward in the field of downy mildew resistance in spinach. The new resistance allele of the invention behaves as a single dominant locus in relation to the resistance it confers to races Pfs:1 Pfs:2, Pfs:3, Pfs:4, Pfs:5, Pfs:6, Pfs:9, Pfs:11, Pfs:12, Pfs:13, Pfs:14, Pfs:15 and isolate UA1014. It can be easily introduced into any other spinach plant, irrespective of the type (e.g. industry-, fresh and Asiatic spinach) or leaf morphology (e.g. savoy, semi-savoy, smooth, and weakly to strongly incised leaves) or any other characteristic, to render it resistant against *Peronospora* isolates Pfs:1 Pfs:2, Pfs:3, Pfs:4, Pfs:5, Pfs:6, Pfs:9, Pfs:11, Pfs:12, Pfs:13, Pfs:14, Pfs:15 and UA1014.

Stacking of the R15 resistance conferring allele of the invention that provides resistance to Pfs:1 Pfs:2, Pfs:3, Pfs:4, Pfs:5, -Pfs:6, Pfs:9, Pfs: 11, Pfs: 12, Pfs:13, Pfs:14, Pfs: 15 and UA1014 with other resistance alleles known in the art and/or with those that will be identified in the future can lead to resistance against all known *Peronospora* races.

Spinach plants of the invention, carrying the new source of resistance designated as R15, can be crossed to other spinach plants carrying one or more resistance genes different from R15, to obtain an even broader resistance to the various *Peronospora* races.

The spinach plants of the invention are obtainable by crossing a first spinach plant with a second spinach plant, wherein one or both of the spinach plants may comprise an R15 resistance allele, to obtain F1 plants and optionally more generations of spinach plants which may comprise the R15 resistance allele.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT INFORMATION

The Deposit with NCIMB Ltd, Ferguson Building, Craibstone Estate, Bucksburn, Aberdeen AB21 9YA, UK, on Oct. 15, 2015, under deposit accession number 42466 was made pursuant to the terms of the Budapest Treaty. Upon issuance of a patent, all restrictions upon the deposit will be removed, and the deposit is intended to meet the requirements of 37 CFR §1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The present invention thus relates to a spinach plant which may comprise a new allele of a resistance gene—R15— which confers resistance to *Peronospora farinosa* f. sp. *spinaciae* races Pfs:1, Pfs:2, Pfs:3, Pfs:4, Pfs:5, Pfs:6, Pfs:9, Pfs: 11, Pfs:12, Pfs:13, Pfs:14, Pfs:15 and isolate UA1014 and does not confer resistance to *Peronospora farinosa* f. sp. *spinaciae* race Pfs:7, and wherein the R15 allele is as found in a plant grown from a seed of which a representative sample was deposited with the NCIMB under NCIMB accession number 42466.

Surprisingly, it was further found that in homozygous state the R15 allele, as found in a plant grown from a seed of which a representative sample was deposited with the NCIMB under NCIMB accession number 42466, also confers resistance to *Peronospora farinosa* f. sp. *spinaciae* race Pfs:8 and at least intermediate resistance to Pfs: 10. It was further found that the R15 allele in heterozygous state confers at least intermediate resistance to *Peronospora farinosa* f. sp. *spinaciae* race Pfs:8 and Pfs: 10.

The presence of the R15 allele in a plant may be detected using a seedling test as described herein. The disease resistance assay shows the phenotype, as illustrated by example 1.

A seedling test is defined as a test wherein spinach plants are planted in trays containing growth medium, optionally fertilized twice a week after seedling emergence. Plants are inoculated at the first true leaf stage with a sporangial suspension having a concentration of approximately $2.5 \times 10^5$/ml of one of the pathogenic races of *Peronospora farinosa* f. sp. *spinaciae* or isolates to be tested. The inoculated plants are placed in a dew chamber at 18° C. with 100% relative humidity for a 24 h period, and then moved to a growth chamber at 18° C. with a 12 h photoperiod for 6 days. After 6 days, the plants are returned to the dew chamber for 24 h to induce sporulation, and subsequently scored for a disease reaction. Preferably, 30 plants per race are tested.

The genotype of the disease resistance can be assayed by testing the inheritance of the resistance gene in a cross with a fully susceptible spinach plant. In an F2 population of such a cross this gene segregates approximately in a 3:1 ratio, i.e. on average 3 out of 4 F2 plants possess the resistance for races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014, as is illustrated by example 2. The R15 resistance conferring allele is thus an allele that upon introduction thereof in a spinach plant that is susceptible to all races of *Peronospora farinosa* f. sp. *spinaciae* induces a resistance profile that at present may comprise resistance to races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014, and optionally to races Pfs:8 and/or Pfs: 10, and a absence of resistance to race Pfs:7. Preferably, the resistance profile consists of resistance to races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014, and optionally to races Pfs:8 and/or Pfs: 10, and an absence of resistance to race Pfs:7. However, it is possible that the R15 allele in the future will be linked to resistance to other races that are at present not yet known, for example because they have not yet been described or identified or do not yet exist. When the R15 allele is found to confer resistance to these future races as well they are considered to be included in the R15 resistance profile as defined herein.

Plants carrying the R15 allele in either homozygous or heterozygous state are resistant to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014.

As used herein, a plant is resistant against an isolate of *Peronospora farinosa* f. sp. *spinaciae* when a plant shows no symptoms in the seedling test described herein.

As used herein, a plant is intermediately resistant against an isolate of *Peronospora farinosa* f. sp. *spinaciae* when a plant shows only symptoms of chlorosis, or sporulation occurring only on the tips of the cotyledons in the seedling test described herein.

When a plant shows more symptoms than described above, such plant is considered susceptible.

With regard to the resistance level against *Peronospora farinosa* f. sp. *spinaciae* race Pfs:8 the F2 of a cross of the plant of the invention carrying the R15 allele homozygously with a plant that is fully susceptible will segregate in a ratio of approximately 1:2:1, i.e. about 25% of the plants are resistant having no symptoms; about 50% of the plants are intermediately resistant, having only symptoms of chlorosis, or sporulation occurring only on the tips of the cotyledons in the seedling test; and about 25% of the plants in the F2 will be fully susceptible.

With regard to the resistance level against *Peronospora farinosa* f. sp. *spinaciae* race Pfs: 10 the F2 of a cross of a plant carrying the R15 allele homozygously with a fully susceptible plant will segregate in a ratio of approximately 3:1, i.e. about 75% of the plants are intermediately resistant, having only symptoms of chlorosis, or sporulation occurring only on the tips of the cotyledons in the seedling test; and about 25% of the plants in the F2 will be fully susceptible.

A plant carrying the R15 resistance conferring allele and no other genetic determinants causing resistance against downy mildew, will score susceptible for *Peronospora farinosa* f. sp. *spinaciae* race Pfs:7 in the seedling test as described herein. This means that such a plant inoculated with Pfs:7 will show more than only symptoms of chlorosis, or sporulation occurring only on the tips of the cotyledons. Sporulation is likely to occur all over the seedling.

The R15 allele may be introduced into any other plant by introgression from a plant grown from a seed of which a representative sample was deposited with the NCIMB on 15 Oct. 2015 under NCIMB accession number 42466 or any other plant derived there from. The deposited seeds may comprise the R15 allele and are thus a source of the allele. The R15 allele may be introduced into other spinach plants as described in example 2 and 3. Spinach plants that carry the same R15 allele as is found in plants grown from seeds deposited under NCIMB accession number 42466 but are not directly obtained therefrom are also plants of the invention.

The invention thus relates to a spinach plant which may comprise an introgressed R15 allele, wherein said allele confers resistance to *Peronospora farinosa* f. sp. *spinaciae* races Pfs: 1, Pfs:2, Pfs:3, Pfs:4, Pfs:5, Pfs:6, Pfs:9, Pfs:11, Pfs:12, Pfs:13, Pfs:14, Pfs:15 and isolate UA1014, and does not confer resistance to *Peronospora farinosa* f. sp. *spinaciae* race Pfs:7, and wherein said allele is as found in a plant grown from a seed of which a representative sample was deposited with the NCIMB under NCIMB accession number 42466.

In particular, the invention relates to a spinach plant which may comprise at least an R15 allele, wherein said allele confers resistance to at least *Peronospora farinosa* f. sp. *spinaciae* races Pfs:1, Pfs:2, Pfs:3, Pfs:4, Pfs:5, Pfs:6, Pfs:9, Pfs: 11, Pfs:12, Pfs:13, Pfs:14, Pfs:15 and isolate UA1014, at least intermediate resistance to races Pfs:8 and Pfs: 10 and does not confer resistance to *Peronospora farinosa* f. sp. *spinaciae* race Pfs:7, and wherein said allele is as found in the genome of a plant grown from a seed of which a representative sample was deposited with the NCIMB under NCIMB accession number 42466.

More in particular, the invention relates to a spinach plant which may comprise at least an R15 allele, wherein said allele confers resistance to at least *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and isolates UA1014 and US1508, at least intermediate resistance to races Pfs:8, Pfs:10 and does not confer resistance to *Peronospora farinosa* f. sp. *spinaciae* race Pfs:7, and wherein said allele is as found in a plant grown from a seed of which a representative sample was deposited with the NCIMB under NCIMB accession number 42466.

As used herein, "introgressed" when used in reference to a genetic locus, e.g. the R15 allele of the invention, refers to a genetic locus that has been introduced either homozygously or heterozygously into a new genetic background, of the same or a different species. Introgression of a genetic locus can thus be achieved through plant breeding methods such as crossing and/or backcrossing and selecting. Selection can take place based on phenotype e.g. by using a disease test, or based on genotype e.g. through the use of molecular markers. Depending on the heritability of a trait, it can be introgressed into another plant in only one generation, for example when the trait is dominant monogenic, but introgression also encompasses a breeding process that takes multiple generations, for example when the trait is recessive and/or involves more than one gene. Introgression is used herein to describe the entire process.

The R15 allele of the invention is located on chromosome 1, and in a plant grown from a seed of which a representative sample was deposited with the NCIMB under NCIMB accession number 42466 the R15 allele is detectable using markers SO00009 and/or SO00010 and/or SO00013 and/or SO00020. When crossing plants that carry the R15 allele with a fully susceptible plant of reference variety Viroflay, the SNPs or indel of these markers as indicated in bold and underlined in SEQ ID No. 1, and/or SEQ ID No. 3, and/or SEQ ID No. 5, and/or SEQ ID No. 7 (see Table 1) are linked to the presence of the R15 allele. In such a cross the SNPs or indel of these markers as indicated in bold and underlined in SEQ ID No. 2, and/or SEQ ID No. 4, and/or SEQ ID No. 6, and/or SEQ ID No. 8 (see Table 1) are linked to the absence of the R15 allele.

Therefore, in one embodiment the invention relates to a spinach plant which may comprise the resistance allele—R15—wherein the allele is located on chromosome 1 and linked to SNP markers as present in SEQ ID No. 1, and/or SEQ ID No. 3, and/or SEQ ID No. 5, and/or SEQ ID No. 7.

The deposit is homozygous for the SNPs and indel of SEQ ID No. 1, and SEQ ID No. 3, and SEQ ID No. 5, and SEQ ID No. 7. When the deposit is crossed with a plant of variety Viroflay these markers are linked to the R15 allele. Therefore, the deposit may function as a reference for the SNPs and indel markers of SEQ ID No. 1, and SEQ ID No. 3, and SEQ ID No. 5, and SEQ ID No. 7. Hence, a plant of variety Viroflay is homozygous for the SNPs and indel of SEQ ID No. 2, and SEQ ID No. 4, and SEQ ID No. 6, and SEQ ID No. 8.

However, the skilled person is aware of the fact that recombination may unlink a marker, in case the marker is not the causal mutation of the trait that it is linked to. Therefore, a plant of the invention which may comprise in its genome the resistance conferring allele of the R15 gene is not limited to the presence of any of the SNPs and indel of SEQ ID No. 1 to 7 as described in Table 1.

In one embodiment the invention relates to the use of a spinach plant which may comprise an R15 resistance allele to develop markers linked to the R15 allele. Such a spinach plant may be, but is not limited to, a plant grown from seed of which a representative sample was deposited with the NCIMB on 15 Oct. 2015 under NCIMB accession number 42466.

In a further embodiment the invention relates to the use of the markers SO000009, SO00010, SO000013, and/or SO000020 as defined in Table 1 to develop new markers that are linked to the R15 allele.

The invention also relates to a method of identifying a spinach plant which may comprise the R15 allele of the invention, the method which may comprise detecting in a spinach plant a marker that is associated with the resistance, wherein the marker is genetically linked within 20 centiMorgan, in particular 15 centiMorgan, more particular 10, even more particular 5, and most particular 1 centiMorgan to markers SO000009, SO00010, SO000013, and/or SO000020 as defined in Table 1. The method may also comprise selecting a plant which may comprise the R15 allele.

In another embodiment, the said method of identifying a spinach plant which may comprise the R15 allele may comprise the step of assaying the resistance by inoculating the plant with a strain of *Peronospora farinosa* f. sp. *spinaciae* Pfs:1, Pfs:2, Pfs:3, Pfs:4, Pfs:5, Pfs:6, Pfs:9, Pfs:11, Pfs:12, Pfs:13, Pfs:14, Pfs:15 and/or isolate UA1014 at the first true leaf stage, optionally including a control plant, and scoring the plants for their disease reaction.

In a further embodiment the said method of identifying a spinach plant which may comprise the R15 allele may comprise the step of assaying the resistance by inoculating the plant with a strain of *Peronospora farinosa* f. sp. *spinaciae* Pfs:8 and/or Pfs:10 at the first true leaf stage, optionally including a control plant, and scoring the plants for their disease reaction.

There are many different marker systems available to the skilled artisan, these include but are not limited to SNPs, AFLP markers, RFLP markers, SSRs, RAPD markers, or isozyme markers. Markers that are genetically linked to or correlated with the R15 allele can be utilized (e.g. Acquaah G., Principles of Plant Genetics and Breeding, 2012, West Sussex UK). Methods to isolate, develop and utilize such markers are known in the art.

As used herein, linkage of two nucleic acid sequences, including a nucleic acid marker sequence and a nucleic acid sequence of an allele such as the R15 allele, may be genetic or physical or both.

In the absence of molecular markers, equivalence of genetic determinants, such as R15 alleles, may be determined by an allelism test. To perform an allelism test, material that is homozygous for the known determinant is crossed with material that is also homozygous for its unknown genetic determinant. When no segregation for the trait to be observed is present in the F2 of the cross, the genetic determinants resulting in the phenotypic trait have been proven to be equivalent or the same. Material with the known genetic determinant, i.e. a plant carrying the R15 allele of the invention and no other genetic determinants providing resistance to *Peronospora*, may for example be a plant grown from seed of which a representative sample was deposited with the NCIMB under NCIMB accession number 42466.

In one aspect the invention relates to a spinach plant which may comprise the R15 allele, obtainable by crossing a spinach plant with a plant grown from a seed of deposit NCIMB 42466 to produce F1 progeny, optionally selfing the F1 progeny to produce F2 progeny and selecting from the F1 and/or F2 progeny the plants that show resistance to at least *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014 and do not show resistance to *Peronospora farinosa* f. sp. *spinaciae* race Pfs:7 as plants having obtained the R15 conferring allele.

The invention further relates to a spinach plant which may comprise the R15 resistance conferring allele, wherein the R15 allele upon introduction thereof in a spinach plant that is susceptible to all races of *Peronospora farinosa* f. sp. *spinaciae* induces a resistance profile that consists of resistance to races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014, and optionally to races Pfs:8 and/or Pfs:10, but wherein the R15 allele does not induce resistance to race Pfs:7.

The word "trait" in the context of this application refers to the phenotype of the plant, in the present invention to a particular resistance profile. A resistance profile is a combination of a number of races or isolates against which the plant shows resistance. In particular, the word "trait" refers to the trait of the invention, more in particular to the resistance to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014. The word "trait" further refers to a resistance profile which may comprise resistance to Pfs:1, Pfs:2, Pfs:3, Pfs:4, Pfs:5, Pfs:6, Pfs:9, Pfs:11, Pfs:12, Pfs:13, Pfs: 14, Pfs:15 and UA1014 and at least intermediate resistance to races Pfs:8 and Pfs: 10 as described herein. The trait of the invention does not comprise resistance to Pfs:7. The term "genetic determinant" is used for the genetic information in the genome of the plant that causes the trait of the invention. When a plant shows the trait of the invention, its genome may comprise the genetic determinant causing the trait of the invention. The plant thus has the genetic determinant of the invention. The word allele and genetic determinant can be used interchangeably, this means that when a plant shows the trait of the invention, its genome may comprise the resistance conferring allele of the R15 gene. A plant showing the trait of the invention may comprise the R15 resistance conferring allele either in homozygous or heterozygous state. As described herein, homozygous or heterozygous presence of the R15 resistance conferring allele influences the expression of the trait of the invention for *Peronospora farinosa* f. sp. *spinaciae* races Pfs:8 and Pfs:10.

It is clear that the parent that provides the trait of the invention is not necessarily a plant grown directly from the deposited seeds. The parent may also be a progeny plant from the seed or a progeny plant from seeds that are identified to have the trait of the invention by other means.

In one embodiment the plant of the invention which may comprise an allele of the resistance gene conferring resistance to *Peronospora farinosa* f. sp. *spinaciae* is an agronomically elite spinach plant.

In the context of this invention an agronomically elite spinach plant is a plant having a genotype that results into an accumulation of distinguishable and desirable agronomic traits which allow a producer to harvest a product of commercial significance.

In the course of breeding a new spinach plant carrying the R15 allele, desirable agronomic traits may be introduced into said spinach plant independently of the R15 allele. As used herein, "desirable traits" include but are not limited to e.g. improved yield, leaf shape, leaf size, leaf number, leaf color, seed number, seed size, plant vigor, plant height, bolting, and resistance to one or more diseases or disease causing organisms. Any one of these desirable traits may be combined with the R15 allele.

In a further embodiment the spinach plant of the invention may be resistant against *Peronospora farinosa* f. sp. *spinaciae* races Pfs: 1-15 and UA1014, due to the presence of another downy mildew resistance gene providing resistance to strains not covered by the R15 gene.

In another embodiment the agronomically elite spinach plant of the invention may be resistant against *Peronospora farinosa* f. sp. *spinaciae* races Pfs:1-15 and UA1014, due to the presence of another downy mildew resistance gene providing resistance to strains not covered by the R15 gene.

In yet a further embodiment the agronomically elite spinach plant of the invention is an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of an $F_1$ hybrid variety.

The invention further relates to propagation material of a spinach plant of the invention, wherein a plant grown or regenerated from the said propagation material is at least resistant to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs: 14, Pfs:15 and UA1014. In one embodiment, the propagation material is suitable for sexual reproduction. Such propagation material may comprise for example a microspore, pollen, ovary, ovule, embryo sac and egg cell. In another embodiment, the propagation material is suitable for vegetative reproduction. Such propagation material may comprise for example a cutting, root, stem, cell, protoplast, and a tissue culture of regenerable cells. A part of the plant that is suitable for preparing tissue cultures is in particular a leaf, pollen, an embryo, a cotyledon, a hypocotyl, a meristematic cell, a root tip, an anther, a flower, a seed and a stem.

The invention further relates to a spinach plant grown or regenerated from the said propagation material of a plant of the invention, which plant is resistant to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014.

The invention further relates to a cell of a spinach plant of the invention, which cell may comprise an R15 allele which leads to resistance to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014, wherein said allele is as present in a spinach plant, representative seeds of which were deposited under NCIMB accession number 42466. The said cell thus may comprise the genetic information encoding the said resistance, in particular genetic information which is substantially identical, preferably completely identical to the genetic information encoding the said resistance trait of the spinach plant, representative seeds of which were deposited under NCIMB accession number 42466, more in particular the R15 allele described herein. Preferably, the cell of the invention is part of a plant or plant part, but the cell may also be in isolated form.

The invention also relates to a cell of a spinach plant of the invention, which cell may comprise an R15 resistance conferring allele which leads to resistance to at least *Peronospora farinosa* f. sp. *spinaciae* races Pfs:1, Pfs:2, Pfs:3, Pfs:4, Pfs:5, Pfs:6, Pfs:9, Pfs: 11, Pfs:12, Pfs:13, Pfs:14, Pfs:15 and UA1014, and which plant is obtained by transferring the *Peronospora farinosa* f. sp. *spinaciae* resistance as found in seeds that were deposited under NCIMB accession number 42466 into an agronomically valuable spinach plant.

The invention further relates to seed of the spinach plant of the invention, which seed may comprise in its genome the genetic information that encodes the resistance trait of the invention. The invention thus relates to seed which may comprise at least one allele of the R15 gene conferring resistance to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014.

The invention also relates to the use of seeds that were deposited under NCIMB accession number 42466 for transferring resistance to at least *Peronospora farinosa* f. sp. *spinaciae* races Pfs: 1, Pfs:2, Pfs:3, Pfs:4, Pfs:5, Pfs:6, Pfs:9, Pfs: 11, Pfs:12, Pfs:13, Pfs:14, Pfs:15 and UA1014 into an agronomically valuable spinach plant by crossing a plant grown from said deposited seed into a plant and crossing this plant with another plant which may comprise other agronomically desirable traits.

The invention also relates to progeny of a spinach plant, which progeny is at least resistant to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs: 14, Pfs:15 and UA1014. Such progeny may be produced by sexual or vegetative reproduction of a plant of the invention or a progeny plant thereof. The progeny plant displays the R15 resistance trait in the same or in a similar way as the plant of which representative seed was deposited (NCIMB 42466). This means that such progeny is at least resistant to Peronospora farinosa f. sp. spinaciae races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014. Progeny that is the result of sexual reproduction may further display resistance to other races of Peronospora farinosa f. sp. spinaciae, e.g. Pfs:7, due to the fact that the one of the parents of the progeny plant may comprise a resistance allele different from R15 which e.g. confers resistance to Pfs:7 and/or other isolates. Such a progeny plant is e.g. described in example 3.

As used herein the word "progeny" is intended to mean the offspring or the first and all further descendants from a cross with a plant of the invention that shows the R15 resistance trait. Progeny of the invention may comprise descendants of any cross with a plant of the invention that carries the R15 resistance trait. Such progeny is for example obtainable by crossing a first spinach plant with a second spinach plant, wherein at least one of the spinach plants was grown from seeds of a plant of the invention, representative seeds of which were deposited with the NCIMB under NCIMB accession number 42466, but may also be the progeny of any other spinach plant which may comprise the R15 allele as present in NCIMB 42466.

The said progeny plants may comprise an introgression fragment that may comprise resistance allele R15, wherein the said introgression fragment is obtainable from a spinach plant of which representative seed is deposited with the NCIMB under NCIMB accession number 42466. The resistance trait thus has a genetic basis in the genome of a spinach plant, and using the assay described in example 1, spinach plants may be identified as being plants of the invention. It is understood that a parent plant that provides the trait of the invention is not necessarily a plant grown directly from the deposited seeds. The parent may also be a progeny plant from the seed, or a progeny plant from seeds that are identified to have (or to have acquired) the trait of the invention by other means. In one embodiment, the invention relates to spinach plants that carry the trait of the invention and that have acquired the said trait by introduction of the genetic information that is responsible for the trait from a suitable source, either by conventional breeding, or genetic modification, in particular by cis-genesis or trans-genesis. Cis-genesis is genetic modification of plants with a natural gene, encoding an (agricultural) trait from the crop plant itself or from a sexually compatible donor plant. Trans-genesis is genetic modification of a plant with a gene from a non-crossable species or with a synthetic gene.

In one embodiment, the source from which the genetic information is acquired is formed by plants grown from the deposited seeds, or by sexual or vegetative descendants thereof. "Progeny" also encompasses plants that carry the trait of the invention which is obtained from other plants of the invention by vegetative propagation or multiplication.

The invention also relates to harvested leaves of spinach plants of the invention, to food products which may comprise harvested leaves of spinach plants of the invention, either in natural or in processed form.

Spinach leaves are sold in packaged form, including without limitation as pre-packaged spinach leaves or as processed in a salad which may comprise spinach leaves. Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach plant of the invention, as well as leaves of spinach plants derived from the invention. The invention further relates to a container which may comprise one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition.

The invention further relates to the use of a spinach plant of the invention in breeding to confer resistance against Peronospora farinosa f. sp. spinaciae.

The invention also relates to the use of the Peronospora farinosa f. sp. spinaciae resistance allele as found in seeds that were deposited under NCIMB accession number 42466 for conferring resistance to Peronospora farinosa f. sp. spinaciae races Pfs:1, Pfs:2, Pfs:3, Pfs:4, Pfs:5, Pfs:6, Pfs:9, Pfs: 11, Pfs: 12, Pfs: 13, Pfs: 14, Pfs: 15 and UA1014 onto a Spinacia oleracea plant.

The invention further relates to the use of a Spinacia oleracea plant as a recipient of Peronospora farinosa f. sp. spinaciae resistance allele as found in seeds that were deposited under NCIMB accession number 42466.

In one aspect the invention relates to a method for production of a spinach plant which is resistant to Peronospora farinosa f. sp. spinaciae races Pfs:1, Pfs:2, Pfs:3, Pfs:4, Pfs:5, Pfs:6, Pfs:9, Pfs: 11, Pfs: 12, Pfs: 13, Pfs: 14, Pfs: 15 and UA1014, which may comprise the following steps: (a) crossing a plant which may comprise the resistance conferring allele of the R15 gene with another plant; (b) selecting plants that have the said resistance allele in the F1; (c) optionally performing one or more rounds of selfing and/or crossing, and subsequently selecting, for a plant which may comprise the resistance conferring allele of the invention. The invention also includes a spinach plant produced by this method.

In another aspect, the invention relates to a method for production of a spinach plant which may comprise resistance to Peronospora farinosa f. sp. spinaciae races Pfs:1, Pfs:2, Pfs:3, Pfs:4, Pfs:5, Pfs:6, Pfs:9, Pfs: 11, Pfs: 12, Pfs: 13, Pfs: 14, Pfs: 15 and UA1014, which may comprise: (a) crossing a plant which may comprise the R15 resistance allele with another plant; (b) optionally selecting for plants that have the said resistance in the F1; (c) optionally backcrossing the resulting F1 with the preferred parent and selecting for plants that have the said resistance in the BC1F1; (d) optionally performing one or more additional rounds of selfing, crossing, and/or backcrossing, and subsequently selecting for a plant which may comprise the said resistance allele or show the resistance profile. The invention also includes a spinach plant produced by this method.

More particular, the invention relates to a method for introgressing the R15 resistance allele into an agronomically elite spinach plant by means of backcrossing, which may comprise: (a) crossing a spinach plant which may comprise the R15 resistance conferring allele with an agronomically elite spinach plant not comprising said allele in its genome to produce F1 progeny; (b) optionally selecting an F1 progeny plant which may comprise said resistance conferring allele; (c) crossing a progeny plant which may comprise the R15 resistance allele with the said agronomically elite spinach plant to produce backcross progeny; and (d) selecting backcross progeny which may comprise the R15 resistance allele; and (e) optionally, repeating steps (c) and (d) one or more times. In particular step (e) is repeated from 1 up to 10 times. The invention also includes a spinach plant produced by this method.

The invention additionally provides a method of introducing a desired trait into an agronomically elite spinach plant which is resistant to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014 due to the presence of the R15 allele, which may comprise: (a) crossing said agronomically elite spinach plant with a second spinach plant that may comprise a desired trait to produce F1 progeny; (b) selecting an F1 progeny plant which may comprise said resistance to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014 and the desired trait; (c) crossing the selected progeny plant with either parent, to produce backcross progeny; (d) selecting backcross progeny which may comprise the desired trait and resistance to *Peronospora farinosa* f. sp. *spinaciae* races Pfs:1, Pfs:2, Pfs:3, Pfs:4, Pfs:5, Pfs:6, Pfs:9, Pfs: 11, Pfs:12, Pfs:13, Pfs: 14, Pfs:15 and UA1014; and (e) optionally repeating steps (c) and (d) one or more times in succession to produce subsequent generations of backcross progeny that may comprise the desired trait and resistance to *Peronospora farinosa* f. sp. *spinaciae* races Pfs: 1, Pfs:2, Pfs:3, Pfs:4, Pfs:5, Pfs:6, Pfs:9, Pfs:11, Pfs:12, Pfs: 13, Pfs:14, Pfs:15 and UA1014. The invention also includes a spinach plant produced by this method.

In one embodiment selection for plants that are resistant to *Peronospora farinosa* f. sp. *spinaciae* races Pfs:1, Pfs:2, Pfs: 3, Pfs:4, Pfs:5, Pfs:6, Pfs:9, Pfs:11, Pfs:12, Pfs:13, Pfs:14, Pfs:15 and UA1014 is done in the F1 or any further generation of a cross or alternatively of a backcross. Selection of plants may be done phenotypically as e.g. described in Example 1.

The invention furthermore relates to a method for producing a hybrid seed which may comprise the R15 resistance allele which may comprise: crossing a first parent plant with a second parent plant and harvesting the resultant hybrid seed, wherein said first parent plant and/or said second parent plant is a plant which may comprise the R15 resistance allele. The invention further relates to a hybrid spinach seed resistant to at least *Peronospora farinosa* f. sp. *spinaciae* races Pfs: 1, Pfs:2, Pfs:3, Pfs:4, Pfs:5, Pfs:6, Pfs:9, Pfs:11, Pfs:12, Pfs:13, Pfs:14, Pfs:15 and UA1014 produced by this method.

In one embodiment, the invention relates to a method for producing a hybrid spinach plant which may comprise the R15 resistance allele, which may comprise crossing a first parent spinach plant with a second parent spinach plant and harvesting the resultant hybrid seed, of which the first parent plant and/or the second parent plant is homozygous for the R15 resistance allele, and growing said hybrid seeds into hybrid plants that are at least resistant to *Peronospora farinosa* f. sp. *spinaciae* races Pfs:1, Pfs:2, Pfs:3, Pfs:4, Pfs:5, Pfs:6, Pfs:9, Pfs: 11, Pfs:12, Pfs:13, Pfs:14, Pfs:15 and UA1014.

In one embodiment a plant produced by the methods described herein that is homozygous for the R15 resistance allele will further be at least resistant to *Peronospora* race Pfs:8 and at least intermediately resistant to *Peronospora* race Pfs: 10. A plant of a hybrid variety which may comprise the R15 resistance allele homozygously, due to the fact that both parents contributed the R15 resistance allele, will thus be at least resistant to *Peronospora* race Pfs:8 and at least intermediately resistant to *Peronospora* race Pfs:10.

In another embodiment a plant produced by the methods described herein which is heterozygous for the R15 resistance allele, e.g. a hybrid wherein only one of the parents contributed the R15 resistance allele, will be at least intermediately resistant to *Peronospora* races Pfs:8 and Pfs: 10.

In another embodiment a plant produced by the methods described herein, which is either heterozygous or homozygous for the R15 resistance allele, will be at least resistant to isolate US1508.

In yet a further embodiment the plant obtained by the methods described herein may comprise, next to the R15 resistance allele, one or more other resistance alleles conferring resistance to *Peronospora farinosa* f. sp. *spinaciae*. This may increase the resistance level of the plant for Pfs:7, Pfs:8 and/or Pfs: 10 depending on the resistance pattern that is conferred by said one or more of these other resistance conferring alleles.

The invention also relates to a method for the production of a spinach plant carrying the R15 resistance allele by using a seed that may comprise said allele in its genome for growing the said spinach plant. The seed is suitably a seed of which a representative sample was deposited with the NCIMB under deposit number NCIMB 42466.

The invention also relates to a method for seed production which may comprise growing spinach plants from seeds of which a representative sample was deposited with the NCIMB under deposit number NCIMB 42466, allowing the plants to produce seeds, and harvesting those seeds. Production of the seeds is suitably done by crossing or selfing.

In one embodiment, the invention relates to a method for the production of a spinach plant carrying the R15 resistance allele of the invention by using tissue culture.

The invention furthermore relates to a method for the production of a spinach plant carrying the R15 resistance allele of the invention by using vegetative reproduction.

In one embodiment, the invention relates to a method for the production of a spinach plant resistant to *Peronospora farinosa* f. sp. *spinaciae* races Pfs:1, Pfs:2, Pfs:3, Pfs:4, Pfs:5, Pfs:6, Pfs:9, Pfs:11, Pfs: 12, Pfs: 13, Pfs:14, Pfs: 15 and UA1014 by using a method for genetic modification to introduce the said trait into the spinach plant.

The invention also relates to a breeding method for the development of spinach plants carrying the R15 resistance allele of the invention wherein germplasm which may comprise said allele is used. Representative seed of said plant which may comprise the genetic determinant and being representative for the germplasm was deposited with the NCIMB under deposit number NCIMB 42466.

The invention provides preferably a spinach plant resistant to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and UA1014, which plant is obtainable by any of the methods herein described, a combination thereof, and/or familiar to the skilled person.

In the context of this application the resistance to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs: 13, Pfs: 14, Pfs:15 and UA1014 is preferably caused by a genetic determinant that is present in the genome of seed of deposit number NCIMB 42466 and which genetic determinant is interchangeably referred to as the R15 allele, R15 resistance conferring allele, and R15 resistance allele.

The invention further involves a method of determining the genotype of a plant of the invention, representative seed of which has been deposited under NCIMB Accession No. 42466, or a first generation progeny thereof, which may comprise obtaining a sample of nucleic acids from said plant and a reference plant not comprising the genetic determinant of the invention and detecting in the nucleic acids of said samples a plurality of polymorphisms. This method may additionally comprise the step of storing the results of detecting the plurality of polymorphisms on a computer readable medium. The plurality of polymorphisms are indicative of and/or give rise to the presence of the R15 resistance allele.

There are various ways of obtaining genotype data from a nucleic acid sample. Genotype data may be gathered which is specific for certain phenotypic traits (e.g. gene sequences), but also patterns of random genetic variation may be obtained to construct a so-called DNA fingerprint. Depending on the technique used a fingerprint may be obtained that is unique for a spinach plant carrying the resistance allele of the invention. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat. No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DarT (or Diversity Arrays Technology), RAD markers (or Restriction site associated DNA markers) (e.g. Baird et al. PloS One Vol. 3 e3376, 2008; Semagn et al. African Journal of Biotechnology Vol. 5 number 25 pp. 2540-2568, 29 Dec., 2006). Nowadays, sequence-based methods are utilizing Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PloS One Vol. 7 number 5: e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species. For example, it is possible to detect polymorphisms for the presence or absence of the R15 resistance conferring allele by comparing the genotype and/or the sequence of a spinach plant carrying the resistance conferring allele, representative seed of which has been deposited under NCIMB Accession No. 42466, with the genotype and/or the sequence of one or more reference plants. The reference plant(s) used for comparison in this example may for example be, but is not limited to, any of the spinach varieties mentioned in table 2 and/or parent lines, ancestor, or progeny plants thereof as.

The polymorphism revealed by these techniques may be used to establish links between genotype and phenotype. The polymorphisms may thus be used to predict or identify certain phenotypic characteristics, e.g. the resistance provided by the R15 resistance conferring allele, individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

The invention is further described by the following paragraphs:

1. A spinach plant comprising an introgressed R15 allele, wherein said allele confers resistance to at least *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014 and does not confer resistance to *Peronospora farinosa* f. sp. *spinaciae* race Pfs:7, and wherein said allele is as found in a plant grown from a seed of which a representative sample was deposited with the NCIMB under NCIMB accession number 42466.

2. The spinach plant of paragraph 1 comprising the R15 allele heterozygously, wherein said plant further has at least intermediate resistance to *Peronospora farinosa* f. sp. *spinaciae* races Pfs:8 and Pfs:10.

3. The spinach plant of paragraph 1 comprising the R15 allele homozygously, wherein the homozygous presence of said allele further confers resistance to *Peronospora farinosa* f. sp. *spinaciae* race Pfs:8 and intermediate resistance to *Peronospora farinosa* f. sp. *spinaciae* race Pfs: 10.

4. The spinach plant as described in of any of the paragraphs 1 to 3, wherein the R15 allele is located on chromosome 1 and wherein the allele in a plant grown from a seed of which a representative sample was deposited with the NCIMB under NCIMB accession number 42466 is linked to the SNPs in SEQ ID No. 1, and/or SEQ ID No. 5, and/or SEQ ID No. 7, as indicated in bold and underlined in table 1 and/or the indel of SEQ ID No. 3, which indel is the part of SEQ ID No. 4 that is indicated that is indicated in bold and underlined in table 1.

5. The spinach plant as described in of any of the paragraphs 1 to 4, wherein the plant is an agronomically elite spinach plant.

6. The agronomically elite spinach plant as described in paragraph 5, wherein said plant is a plant of an inbred line or a hybrid plant.

7. The spinach plant as described in any of the paragraphs 1 to 6, wherein the spinach plant is further resistant to *Peronospora farinosa* f. sp. *spinaciae* race Pfs:7.

8. A propagation material capable of developing into and/or being derived from a spinach plant as defined in any of the paragraphs 1 to 7, wherein the propagation material comprises the genetic determinant of paragraph 1 and wherein the propagation material comprises a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.

9. A cell of a spinach plant, wherein the cell comprises the R15 allele of paragraph 1, wherein the said R15 allele is as present in a spinach plant, representative seeds of which were deposited under NCIMB accession number 42466.

10. A spinach seed comprising in its genome at least the R15 allele of paragraph 1.

11. The seed of paragraph 10, wherein the seed gives rise to an agronomically elite spinach plant.

12. One or more harvested leaves of the spinach plant as defined in any of the paragraphs 1 to 7.

13. A food product comprising the one or more harvested leaves of paragraph 12.

14. A container comprising the one or more harvested leaves of paragraph 12.

15. A container comprising one or more spinach plants as described in any of the paragraphs 1 to 7, optionally in a growth substrate for harvest of leaves from the one or more spinach plants.

16. Use of the spinach plant as described in any of the paragraphs 1 to 7, in breeding to confer resistance against *Peronospora farinosa* f. sp. *spinaciae* to a spinach plant.

17. Use as described in paragraph 16, wherein the resistance against *Peronospora farinosa* f. sp. *spinaciae* comprises resistance against races covered by the resistance profile of the R15 allele.

18. Use as described in paragraph 17, wherein the resistance profile comprises resistance to at least *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014 but not to race Pfs:7.

19. Use of the spinach plant as described in any of the paragraphs 1 to 7 to develop markers linked to the R15 allele as described in paragraph 1.

20. Use of the markers SO00009, SO00010, SO00013, and/or SO00020, as defined in table 1, to develop markers linked to the R15 allele.

21. A method of identifying a spinach plant comprising the R15 allele of paragraph 1, the method comprising detecting in a spinach plant a marker that is associated with the resistance, wherein the marker is genetically linked within 20 centiMorgan, in particular 15 centiMorgan, more in particular 10, even more particular 5, and most particular 1 centiMorgan to markers SO00009, SO00010, SO00013, and/or SO00020 as defined in table 1.

22. The method of paragraph 21, further comprising the step of assaying the resistance by inoculating the spinach plant with a strain of *Peronospora farinosa* f. sp. *spinaciae* race Pfs:1, Pfs:2, Pfs:3, Pfs:4, Pfs:5, Pfs:6, Pfs:9, Pfs:11, Pfs:12, Pfs:13, Pfs:14, Pfs:15 and/or isolate UA1014 at the first true leaf stage, optionally including a control plant, and scoring the plants for their disease reaction.

23. The method of paragraph 21, further comprising the step of assaying the resistance by inoculating the spinach plant with a strain of *Peronospora farinosa* f. sp. *spinaciae* race Pfs:8 and/or Pfs:10 at the first true leaf stage, optionally including a control plant, and scoring the plants for their disease reaction.

24. A method of selecting a spinach plant comprising the R15 allele, comprising performing the method as described in any of the paragraphs 21 to 23 and selecting a plant showing no symptoms, or only symptoms of chlorosis, or sporulation occurring only on the tips of the cotyledons in a seedling test, and/or comprising a marker associated with the resistance, as a plant comprising the R15 allele.

25. A method for producing a spinach plant comprising resistance to *Peronospora farinosa* f. sp. *spinaciae* Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014, comprising: (a) crossing a plant comprising the resistance allele of claim 1, with another plant; (b) performing one or optionally more rounds of selfing and/or crossing; (c) optionally selecting after each round of selfing or crossing for a plant that comprises said resistance.

26. A method of producing a hybrid spinach seed comprising crossing a first parent spinach plant with a second parent spinach plant and harvesting the resultant hybrid spinach seed, wherein said first parent spinach plant and/or said second parent spinach plant comprises the R15 allele of paragraph 1.

27. A method of determining the genotype of a spinach plant comprising the R15 allele of paragraph 1, or a first, second or third generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein one or more of the detected polymorphisms are indicative of the presence of the R15 allele of paragraph 1.

28. The method of paragraph 27 additionally comprising the step of storing the results of detecting the plurality of polymorphisms on a computer readable medium, or transmitting the results of detecting the plurality of polymorphisms.

29. The spinach plant of paragraph 1, which is a plant grown from seed having been deposited under NCIMB accession No. 42466.

TABLE 1

| Marker name | Seq ID No. | Sequence marker |
| --- | --- | --- |
| SO00009 | SEQ ID No:1 | GAGGTGGTTATGGAGGAG TACACAACAAGGTA<u>C</u>ACT TCACATCTCCACCACCCCC TTCATTCCATACCGAAAA CTTGCC |
|  | SEQ ID No:2 | GAGGTGGTTATGGAGGAG TACACAACAAGGTA<u>A</u>ACT TCACATCTCCACCACCCCC CTTCATTCCATACCGAAAA CTTGCC |

TABLE 1-continued

Marker information

| Marker name | Seq ID No. | Sequence marker |
|---|---|---|
| SO00010 | SEQ ID No:3 | GCTCAGTGTCATCTTTAT GCAGAAGTATATCATAGA ATTGTCAAAAAATGATCC GATCTAGACCAACCTGATA AAAAAAATCGGAAGTGGC TTGATCTCG |
|  | SEQ ID No:4 | GCTCAGTGTCATCTTTAT GCAGAAGTATATCATAGAA TTGTCAAAAAATGATCCGAT CGATCTAGACCAACCTGAT AAAAAAAATCGGAAGTGG CTTGATCTCG |
| SO00013 | SEQ ID No:5 | GCAGCATGATTGACAACTT GGTTTAACTTTTGCTGCN ANANCTCTTTTTTCTTTCTT GTATCCTCTTTTAACTTCCAT TCAAAAAGAATTTTGTGGTT TAGGAGTTGTAGTGGTGGGGT |
|  | SEQ ID No:6 | GCAGCATGATTGACAACTT GGTTTAACTTTTGCTGCNAN ANCTCTTTTTTCTTTCTTGTAT CCTCTTTTAACTTCCATCCAA AAAGAATTTTGTGGTTTAGG AGTTGTAGTGGTGGGGT |
| SO00020 | SEQ ID No:7 | GTCGATCTGACAAGTTTGA GATGTATAAGTTTTTCTA GGGATCAATTTNGTATCA AATGAGCGGTTTAATTTCA AGTCTTGTAATCAAATAAA AGTCTGATTTTGTCAAATCTA TCAAAATCATAAACAAATA TCAAGAGATG |
|  | SEQ ID No:8 | GTCGATCTGACAAGTTTGA GATGTATAAGTTTTTCTAGG GATCAATTTNGTATCAAAT GAGCGGTTTAATTTCAAGT CGTGTAATCAAATAAAGT CTGATTTTGTCAAATCTATC AAAATCATAAACAAATATC AAGAGATG |

SEQ ID No:1, SEQ ID No:3, SEQ ID No:5 and SEQ ID No:7 represent the alleles of markers SO00009, SO00010, SO00013, SO00020 that in the genome of seeds of the deposit NCIMB 42466 are linked to R15 resistance allele of the invention. The sequences of SEQ ID No:2, SEQ ID No:4, SEQ ID No:6 and SEQ ID No:8 represent the wildtype alleles for the molecular markers SO00009, SO00010, SO00013, SO00020 as present in the fully susceptible reference variety Viroflay, respectively.

The nucleotides that are different between the marker allele linked to the R15 allele and the marker allele linked to the susceptible allele in a plant of reference variety Viroflay are underlined and in bold. SEQ ID No. 1-2 and 5-8 are SNP markers. In SEQ ID No. 3 the CGAT motive as present in SEQ ID No. 4 is deleted, therefore nothing is highlighted in SEQ ID No. 3, i.e. the marker for SEQ ID No. 3 and 4 is an indel.

The SNPs and indel indicated in these sequences (the nucleotides in bold and underlined and the CGAT indel for SEQ IDs No. 3 and 4) can be used as molecular markers for detecting the presence of the R15 resistance conferring allele in the progeny of a cross between a plant of reference variety Viroflay and a plant comprising the R15 resistance allele, which plant may be a plant grown from a seed of which a representative sample was deposited with the NCIMB under NCIMB accession number 42466.

Example 1

Testing for the R15 Resistance Trait in Spinach Plants

The resistance to downy mildew infection was assayed as described by Irish et al. (2008; Phytopathol. 98: 894-900; seedling test described on pages 895-896), using the differential set shown in Table 2. Spinach plants of the invention carrying the R15 allele homozygously and heterozygously, together with positive and negative control plants, were planted in trays containing Scotts Red-Earth medium, and fertilized twice a week after seedling emergence with Osmocote Peter's (13-13-13) fertilizer (Scotts). Plants were inoculated at the first true leaf stage with a sporangial suspension ($2.5 \times 10^5$/ml) with one of the pathogenic races of *Peronospora farinosa* f. sp. *spinaciae* to be tested. For each of the four accessions 30 plants per race were tested.

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants for this specific test were scored as resistant, intermediately resistant, or susceptible based on symptoms of chlorosis and signs of pathogen sporulation on the cotyledons and true leaves. Plants exhibiting no evidence of chlorosis and sporulation were in this specific test considered as resistant. Resistant plants were re-inoculated to assess whether plants initially scored as resistant had escaped infection, or whether they were truly resistant. Plants that showed only symptoms of chlorosis, or sporulation occurring only on the tips of the cotyledons were scored as intermediately resistant. Plants showing more than these symptoms of downy mildew infection were scored as being susceptible.

In this manner, the 15 officially recognized pathogenic races and isolate UA1014 were tested. The results of this disease test are added to table 2 which further shows the differential set of spinach downy mildew races and the resistance of various spinach varieties (hybrids) to each one of these pathogenic races, together with the parental lines of hybrid variety Lion and a parental line carrying the R6 gene.

A susceptible reaction is scored as "+" (indicating a successful infection by the *Peronospora* strain, with sporulation occurring on the entire cotyledon). Resistance is depicted as "−" (absence of sporulation on the cotyledons). An intermediate resistance response is indicated as "(−)". R6 is a line exhibiting the resistance as described in U.S. patent application Ser. No. 13/774,633.

Comparison of the parental lines of Lion to hybrid variety Lion itself reveals that the broad resistance pattern of Lion results from the combination of at least two resistance genes, coming from either of the parents, because both parents only possess parts of the resistance profile of the hybrid (Lion) that results from the crossing of these two lines. The genetic basis of the resistance in Lion is thus multigenic in nature, caused by the stacking of at least two resistance genes in the hybrid variety, and hence the genetic basis of the *Peronospora* resistance in Lion is entirely different from that in plants of the present invention.

In contrast, the R15 resistance to *Peronospora* races Pfs:1, Pfs:2, Pfs:3, Pfs:4, Pfs:5, Pfs:6, Pfs:9, Pfs: 11, Pfs:12, Pfs:13, Pfs:14, Pfs:15 and isolate UA1014 of the present invention is conferred in a monogenic dominant fashion, which has the great advantage that the R15 resistance allele may be easily transferred to other spinach varieties by crossing/introgression, and may be easily combined with other resistance genes or alleles. When combined with selected other genes or alleles that e.g. confer resistance to downy mildew races Pfs7, Pfs8 and Pfs10, the R15 trait can be used to provide resistance to all downy mildew races known to date in spinach.

In Table 2 the differential set of spinach downy mildew races and the resistance of various spinach varieties (hybrids) to each one of these pathogenic races, together with the parental lines of hybrid variety Lion and a parental lines carrying the R6 and R15 gene are given, as well as a plant carrying the R15 allele heterozygously. A susceptible reaction is scored as "+" (indicating a successful infection by the *Peronospora* strain, with sporulation occurring on the entire cotyledon). Resistance is depicted as "−" (absence of sporulation on the cotyledons). An intermediate resistance response is indicated as "(−)".

TABLE 3-continued

| R15 genotype of tested plants | *Peronospora* race/strain | − | (−) | + |
|---|---|---|---|---|
| Homozygous for R15 | Pfs:11 | 28 | 0 | 0 |
| Heterozygous for R15 | | 30 | 0 | 0 |
| Homozygous for R15 | Pfs:12 | 29 | 0 | 0 |
| Heterozygous for R15 | | 29 | 0 | 0 |
| Homozygous for R15 | Pfs:13 | 30 | 0 | 0 |
| Heterozygous for R15 | | 29 | 0 | 0 |
| Homozygous for R15 | Pfs:14 | 28 | 0 | 0 |
| Heterozygous for R15 | | 30 | 0 | 0 |
| Homozygous for R15 | Pfs:15 | 30 | 0 | 0 |
| Heterozygous for R15 | | 30 | 0 | 0 |
| Homozygous for R15 | UA1014 | 30 | 0 | 0 |
| Heterozygous for R15 | | 30 | 0 | 0 |

TABLE 2

| Races/plants | Viroflay | Resistoflay | Califlay | Clermont | Campania | Boeing | Lion | Lazio | Whale | Polka | Pigeon | Lion male parent | Lion female parent | R6 line | R15 homozygous | R15 heterozygous |
|---|---|---|---|---|---|---|---|---|---|---|---|---|---|---|---|---|
| Pfs:1 | + | − | − | − | − | − | − | − | − | − | − | − | − | − | − | − |
| Pfs:2 | + | − | + | − | − | − | − | − | − | − | − | − | + | − | − | − |
| Pfs:3 | + | + | − | − | − | − | − | − | − | − | − | − | − | − | − | − |
| Pfs:4 | + | + | + | − | − | − | − | − | (−) | + | − | − | + | − | − | − |
| Pfs:5 | + | + | − | + | − | − | − | − | − | − | − | − | − | − | − | − |
| Pfs:6 | + | + | + | + | + | − | − | − | (−) | + | − | − | + | − | − | − |
| Pfs:7 | + | + | + | + | − | − | − | − | (−) | + | − | − | + | + | + | + |
| Pfs:8 | + | + | + | + | + | + | − | − | − | − | − | − | − | + | − | (−) |
| Pfs:9 | + | + | − | + | + | − | − | − | − | − | − | − | − | − | − | − |
| Pfs:10 | + | + | + | + | + | + | + | − | + | + | − | + | + | + | (−) | (−) |
| Pfs:11 | + | + | − | + | − | − | − | + | − | − | − | − | − | − | − | − |
| Pfs:12 | + | + | − | + | + | + | − | + | − | − | − | + | − | − | − | − |
| Pfs:13 | + | + | + | + | (−) | − | − | + | + | (−) | − | − | (−) | − | − | − |
| Pfs:14 | + | + | − | + | + | + | − | + | (−) | − | + | + | − | − | − | − |
| Pfs:15 | + | + | + | − | − | − | − | − | + | + | − | − | + | − | − | − |
| UA1014 | + | + | + | + | + | + | + | + | + | + | + | + | + | (−) | − | − |
| US1508 | + | + | − | − | − | − | − | − | − | − | + | − | − | + | − | − |

In Table 3 the individual disease test scores of an R15 homozygous genotype and an R15 heterozygous genotype against each *Peronospora* race are summarized as obtained in a typical seedling test in which 30 seeds were sown. In those cases where the total number of seedlings does not add up to 30, some seeds have not germinated. Resistance levels are indicated in a similar fashion as for Table 2.

TABLE 3

| R15 genotype of tested plants | *Peronospora* race/strain | − | (−) | + |
|---|---|---|---|---|
| Homozygous for R15 | Pfs:1 | 30 | 0 | 0 |
| Heterozygous for R15 | | 29 | 0 | 0 |
| Homozygous for R15 | Pfs:2 | 27 | 0 | 0 |
| Heterozygous for R15 | | 30 | 0 | 0 |
| Homozygous for R15 | Pfs:3 | 30 | 0 | 0 |
| Heterozygous for R15 | | 30 | 0 | 0 |
| Homozygous for R15 | Pfs:4 | 28 | 0 | 0 |
| Heterozygous for R15 | | 29 | 0 | 0 |
| Homozygous for R15 | Pfs:5 | 30 | 0 | 0 |
| Heterozygous for R15 | | 29 | 0 | 0 |
| Homozygous for R15 | Pfs:6 | 28 | 0 | 0 |
| Heterozygous for R15 | | 30 | 0 | 0 |
| Homozygous for R15 | Pfs:7 | 0 | 0 | 30 |
| Heterozygous for R15 | | 0 | 0 | 30 |
| Homozygous for R15 | Pfs:8 | 29 | 0 | 0 |
| Heterozygous for R15 | | 25 | 4 | 0 |
| Homozygous for R15 | Pfs:9 | 29 | 0 | 0 |
| Heterozygous for R15 | | 30 | 0 | 0 |
| Homozygous for R15 | Pfs:10 | 26 | 4 | 0 |
| Heterozygous for R15 | | 22 | 6 | 0 |

Example 2

Introduction of the R15 Resistance Trait into Other Spinach Plants

A plant of the invention was crossed with a plant that did not contain the R15 resistance trait, to obtain an F1. Thirty plants of the F1 population were tested for resistance to *Peronospora* race UA1014, as described in example 1. This particular resistance was absent from the plant not containing the R15 trait used in the said cross. All 30 plants showed the resistance pattern of the invention, i.e. resistance to pathogenic race UA1014. This demonstrated that the inheritance of R15 resistance allele in relation to UA1014 is comparable to a dominant pattern of inheritance.

In another experiment, a plant of the invention was crossed with a different spinach plant that did not contain the R15 resistance trait of the invention. Plants of the F1 population were selfed, and a total of 112 plants of the F2 generation were tested for *Peronospora* resistance, as described in example 1. As a positive discriminator for the presence of the R15 trait, resistance to UA1014 was assayed, because this resistance was present in the mother plant (R15) but not in the father plant of the cross.

It was observed that UA1014 resistance provided by the R15 allele segregated in the F2 generation in a fashion that corresponds to a dominant monogenic inheritance: 87 of the 112 F2 plants exhibited resistance to UA1014. Table 4 gives a detailed overview of the segregation of the R15 resistance trait in four F2 populations. Chi-square tests confirmed that the observed segregation in the F2 populations was consistent with a 3:1 segregation of the R15 resistance profile, as assayed here with resistance to UA1014.

In Table 4 segregation of the R15 resistance profile in 4 F2 populations from a cross between a spinach plant of the invention and plant of a different genotype, lacking the R15 resistance trait is shown.

TABLE 4

| Population | | R15 present (UA1014 resistant) | R15 absent (UA1014 susceptible) | Total | Chi-square | >0.05? |
|---|---|---|---|---|---|---|
| 1 | Observed | 24 | 6 | 30 | 0.4 | Yes |
|   | Expected | 22.5 | 7.5 | 30 | | |
| 2 | Observed | 23 | 5 | 28 | 0.762 | Yes |
|   | Expected | 21 | 7 | 28 | | |
| 3 | Observed | 19 | 5 | 24 | 0.222 | Yes |
|   | Expected | 18 | 6 | 24 | | |
| 4 | Observed | 21 | 9 | 30 | 0.4 | Yes |
|   | Expected | 22.5 | 7.5 | 30 | | |

Chi-square tests confirm that the observed numbers of F2 plants that were resistant and susceptible were in agreement with what is expected when the trait segregates in a dominant monogenic fashion for resistance to UA1014, namely 3:1 (resistant:susceptible). In all cases Chi-square values are well above 0.05.

Similar results were obtained when the progeny of a cross between a plant that carries the R15 resistance trait and a plant not carrying the said trait were assayed for other the *Peronospora* races to which the R15 allele shows a pattern of dominant inheritance: Pfs:1, Pfs:2, Pfs:3, Pfs:4, Pfs:5, Pfs:6, Pfs:9, Pfs:11, Pfs:12, Pfs: 13, Pfs: 14, Pfs:15 and isolate US1508.

Example 3

Introduction of the R15 Resistance Allele into an Elite Parent Line of Hybrid Variety Lion The R15 allele was introduced in an agronomically elite parent line and corresponding hybrid by backcrossing according to the following steps:
a) A plant homozygous for the R15 allele was crossed as father with a plant of the mother line of Lion. Table 2 shows that the mother line of hybrid variety Lion is susceptible for Pfs:7.
b) Subsequently, a plant of the F1 was crossed with a plant of the mother line of Lion to produce BC1 seed.
c) BC1 seed was grown into BC1F1 plants these plants were tested for resistance to UA1014 as described in example 1.
d) A BC1F1 plant was selected based on the presence of the resistance and the presence of favorable traits of the recurrent parent and crossed again with the recurrent parent, a plant of the mother line of Lion, to produce BC2F1 seeds.
e) Steps (c) and (d) were repeated 2 more times to produce BC4F1 plants
f) A BC4F1 plant was selfed to produce BC4F2 seed.
g) BC4F2 seeds were germinated to produce BC4F2 plants. These plants were tested for resistance against UA1014. Susceptible plants were discarded and the resistant plants were selfed to obtain BC4F3 seeds and subsequent plants. Per crossing populations of plants were tested again for resistance to UA1014. Plants from a BC4F3 population that showed no segregation for resistance to UA1014 were considered to be homozygous for the R15 allele. The BC4F3 plants homozygous for R15 and having the favorable traits of the recurrent parent may serve as a new agronomically elite parent line for making new spinach hybrid varieties.
h) A plant as obtained in step g) was subsequently crossed with a plant of the father line of hybrid variety Lion. Plants resulting from this cross can be regarded as an improved hybrid variety resembling Lion but now resistant to Pfs:1-15 and UA1014.

Example 4

Marker-Based Selection of the R15 Allele

A plant homozygous for the R15 allele was crossed as father with a plant of reference variety Viroflay. Viroflay is fully susceptible for all *Peronospora* races and isolates indicated in Table 2.

Subsequently a plant of the F1 was selfed to produce F2 offspring. Plants of the F2 were sampled for their DNA. The sampled DNA of these plants was subsequently screened with the SO0009 SNP marker using standard molecular marker techniques. Approximately 75% of the plants showed the presence of SEQ ID No. 1, which correlates with the presence of the R15 allele of the invention. The remaining plants of the F2 population only showed the presence of the SNP as present in SEQ ID No. 2, indicating that these plants do not comprise the R15 resistance allele.

In order to confirm the correlation of the SNP in SEQ ID No. 1 with the presence of the R15 allele all plants of the F2 population were subjected to a seedling test using strain UA1014. The results of the seedling test correlated completely with the marker results. All plants resistant to UA1014 showed the presence of the SNP as present in SEQ ID No. 1, while all plants susceptible to UA1014 only showed the presence of the SNP as present in SEQ ID No. 2.

Similar results were obtained for markers SO00010, SO00013, and SO00020.

Having thus described in detail preferred embodiments of the present invention, it is to be understood that the invention is not to be limited to particular details set forth in the above description as many apparent variations thereof are possible without departing from the spirit or scope of the present invention.

The invention claimed is:

1. A method of identifying a spinach plant comprising an R15 allele, wherein said allele confers resistance to at least *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014 and does not confer resistance to *Peronospora farinosa* f. sp. *spinaciae* race Pfs:7, and wherein said allele is as found in a plant grown from a seed of which a representative sample was deposited with the NCIMB under NCIMB accession number 42466, the method comprising detecting in a spinach plant a marker that is associated with the resistance, wherein the marker is genetically linked within 20 centiMorgan, in particular 15 centiMorgan, more in particular 10, even more particular 5, and most particular 1 centiMorgan to at least one marker selected from the group consisting of SEQ ID No. 1, SEQ ID No. 3, SEQ ID No. 5 and SEQ ID No. 7.

2. The method of claim 1, further comprising assaying the resistance by inoculating the spinach plant with at least one strain of *Peronospora farinosa* f. sp. *spinaciae* selected from the group consisting of races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014 at the first true leaf stage, optionally including a control plant, and scoring the plant for its disease reaction.

3. The method of claim 1, further comprising assaying the resistance by inoculating the spinach plant with a strain of *Peronospora farinosa* f. sp. *spinaciae* race Pfs:8 and/or Pfs:10 at the first true leaf stage, optionally including a control plant, and scoring the plant for its disease reaction.

4. A method for producing a spinach plant comprising resistance to *Peronospora farinosa* f. sp. *spinaciae* Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014, comprising: (a) crossing a spinach plant comprising an introgressed R15 allele, representative seed of which was deposited under NCIMB accession number 42466, with another plant; (b) performing one or optionally more rounds of selfing and/or crossing; (c) selecting after each round of selfing or crossing for a plant that comprises said allele.

5. A method of producing a hybrid spinach seed comprising crossing a first parent spinach plant with a second parent spinach plant and harvesting the resultant hybrid spinach seed, wherein said first parent spinach plant and/or said second parent spinach plant is a spinach plant comprising an introgressed R15 allele, representative seed of which was deposited under NCIMB accession number 42466.

6. The method of claim 1, wherein the marker is genetically linked within 15 centiMorgan to markers SO00009, SO00010, SO00013, and/or SO00020 as defined in table 1.

7. The method of claim 6, wherein the marker is genetically linked within 10 centiMorgan to markers SO00009, SO00010, SO00013, and/or SO00020 as defined in table 1.

8. The method of claim 7, wherein the marker is genetically linked within 5 centiMorgan to markers SO00009, SO00010, SO00013, and/or SO00020 as defined in table 1.

9. The method of claim 8, wherein the marker is genetically linked within 1 centiMorgan to markers SO00009, SO00010, SO00013, and/or SO00020 as defined in table 1.

* * * * *